US006861070B1

(12) United States Patent  
Yoshinaga

(10) Patent No.: US 6,861,070 B1  
(45) Date of Patent: Mar. 1, 2005

(54) MEDICINAL COMPOSITIONS FOR TREATING EVACUATORY INSUFFICIENCY

(75) Inventor: Kouji Yoshinaga, Tokyo (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/720,301

(22) PCT Filed: Jun. 23, 1999

(86) PCT No.: PCT/JP99/03343

§ 371 (c)(1),
(2), (4) Date: Mar. 7, 2001

(87) PCT Pub. No.: WO00/00187

PCT Pub. Date: Jan. 6, 2000

(30) Foreign Application Priority Data

Jun. 26, 1998 (JP) ............................................ 10-179497

(51) Int. Cl.$^7$ ........................... A61K 9/20; A61K 9/14; A61K 9/16; A61K 9/56; A61K 38/00

(52) U.S. Cl. ........................ 424/464; 424/489; 424/490; 514/15

(58) Field of Search ................................. 424/464, 489, 424/490; 514/15

(56) References Cited

U.S. PATENT DOCUMENTS

| | | | |
|---|---|---|---|
| 4,703,063 A | 10/1987 | Imai et al. | .................. 514/603 |
| 4,987,152 A | 1/1991 | Imai et al. | .................. 514/603 |
| 5,843,472 A | 12/1998 | Ma et al. | ..................... 424/449 |
| 6,071,882 A | * 6/2000 | Engel et al. | ................... 514/15 |

FOREIGN PATENT DOCUMENTS

| | | |
|---|---|---|
| CA | 1282077 | 3/1992 |
| EP | 0 034 432 | 4/1984 |
| EP | 0 416 804 | 3/1991 |
| EP | 0 194 838 B1 | 6/1993 |
| EP | 799619 A2 | 10/1997 |
| EP | 1020190 A2 | 7/2000 |
| JP | 56-110665 | 9/1981 |
| JP | 62-114952 | 5/1987 |
| JP | 3-24014 A | 2/1991 |
| JP | 2000-169373 | 6/2000 |
| JP | 2001-114679 | 2/2001 |
| JP | 2001-288115 | 10/2001 |
| WO | WO 98/24791 A1 | 6/1998 |
| WO | WO 00/00187 A1 | 1/2000 |

OTHER PUBLICATIONS

MC Michel et al., "Comparison of tamsulosin efficacy in subgroups of patients with lower urinary tract symptoms", Prostate Cancer and Prostatic Diseases, vol. 1 (1998), pp. 332–335.

P. Abrams et al., "A dose–ranging study of the efficacy and safety of tamsulosin, the first prostate–selective $\alpha_{1A}$–adrenoceptor antagonist*, in patients with benign prostatic obstruction (symptomatic benign prostatic hyperplasia)", British Journal of Urology, vol. 80, (1997), pp. 587–596.

J.M. Buzelin et al., "Comparison of tamsulosin with alfuzosin in the treatment of patients with lower urinary tract symptoms suggestive of bladder outlet obstruction (symptomatic benign prostatic hyperplasia)", British Journal of Urology, vol. 80 (1997), pp 597–605.

P. Abrams et al., "Tamsulosin, a selective $\alpha_{1c}$–adrenoceptor* antagonist: a randomized, controlled trial in patients with benign prostatic 'obstruction' (symptomatic BPH)", British Journal of Urology, vol. 76 (1995), pp. 325–336.

Kosaku Yasuda et al., "The Effect of Urapidil on Neurogenic Bladder: A Placebo Controlled Double–Blind Study", The Journal of Urology, vol. 156, pp. 1125–1130, Sep. 1996.

Michel Perrigot et al., "Effect of Intravenous Alfuzosin on Urethral Pressure in Patients with Neurogenic Bladder Dysfunction", Neurourology and Urodynamics vol. 15, pp. 119–131 (1996).

Seigo Hiraga et al., "Usefulness and Safety of Bunazosin Hydrochloride in Neurogenic Bladder After Prolonged Administration", Hinyokika Kito. Acta Urologica Japonica, vol. 38, No. 2, pp. 255–263 (1992).

Yukie Takimoto et al., "Clinical Effect of New α–Adrenergic Blocker on Micturition Disturbance of Neurogenic Bladder and Lower Urinary Tract Obstruction", Hinyokika Kito. Acta Urologica Japonica, vol. 29, No. 2, pp. 255–263, 1983.

Momokazu Gotoh et al., "Effects of Alpha–1–Blocking Agent in the Treatment of Detrusor Sphincter Dyssynergia", Nippon Hinyokika Gakkai Zasshi.Japanese Journal or Urology, vol. 81, No. 12, pp. 1877–1883 (1990).

Martin C. Michel et al., "Tamsulosin: Real Life Clinical Experience in 19,365 Patients", European Urology, vol. 34 (suppl 2) (1998), pp. 37–45.

C. de Mey et al., "A Double–Blind Comparison of Terazosin and Tamsulosin on Their Differential Effects on Ambulatory Blood Pressure and Noctural Orthostatic Stress Testing", European Urology, vol. 33 (1998), pp. 481–488.

C.R. Chapple et al., "Tamsulosin 0.4 mg Once Daily: Tolerability in Older and Younger Patients with Lower Urinary Tract Symptoms Suggestive of Benign Prostatic Obstruction (Symptomatic BPH)", European Urology, vol. 32 (1997), pp. 462–470.

(List continued on next page.)

*Primary Examiner*—Alton N. Pryor
(74) *Attorney, Agent, or Firm*—Finnegan, Henderson, Farabow, Garrett & Dunner, L.L.P.

(57) ABSTRACT

A therapeutic agent for voiding dysfunction associated with neurogenic bladder where said agent contains tamsulosin or a pharmaceutically acceptable salt thereof.

3 Claims, No Drawings

OTHER PUBLICATIONS

S. Kondo et al., "Quantitative Analysis of Adrenergic Alpha–1 and Alpha–2 Receptors in Human Prostatic Urethral Tissue," *British Journal of Urology*, vol. 72, (1993), pp. 68–73.

USP Dictionary of USAN and International Drug Names (1997), p. 689.

U.S. Appl. No. 10/470,550, filed Jul. 30, 2003, Shimoyama et al.

Fitspatrick, J.M. Facts and future lines of research in lower urinary tract imptoms in men and women: an overview of the role of $\alpha_1$–Adrenoceptor antagonists. BJU International, 85 (Suppl. 2), pp. 1–5 (2000).

Williams, T.J., et al., In Vitro $\alpha_1$–adrenoceptor pharmacology of Ro 70–0004 and RS–100329, novel $\alpha_{1A}$–Adrenoceptor selective antagonists. British Journal of Pharmacology, 127, pp. 252–258 (1999).

* cited by examiner

MEDICINAL COMPOSITIONS FOR TREATING EVACUATORY INSUFFICIENCY

This application is a 371 of PCT/JP99/03343 filed Jun. 23, 1999.

TECHNICAL FIELD

The present invention relates to a pharmaceutical agent and, more particularly, it relates to a therapeutic agent for voiding dysfunction associated with neurogenic bladder.

BACKGROUND ART

Bladder and urethra which are called lower urinary tracts participate in a voiding function and the function is governed by the three types of nerves—sympathetic nerve, parasympathetic nerve and somatic nerve (pudendal nerve). Sympathetic nerve participates in accumulation of urine while parasympathetic nerve participates in urination and pudendal nerve is always active during accumulation of urine showing an action of closing the external urethra sphincter muscle (cf. *Rinsho to Kankyu*, 71(5):1180, 1994).

There are various diseases which cause the urinary dysfunction and main ones are classified into (1) neurogenic bladder caused by cerebrospinal disease, cerebrovascular accident, diabetes mellitus, peripheral nervous disturbance, etc., (2) organic lower urinary tract obstruction such as benign prostatic hyperplasia and urethral stricture and (3) contraction insufficiency of bladder caused by stress urinary incontinence in adult females, prostatitis, prostatic cancer and anticholinergic agents as well as others which are called LUTS and there are various mechanism for onset of urinary dysfunction depending upon the disease for the cause (cf. *Rinsho to Yakubutsu Chiryo*, 14(4):304, 1995).

For example, in urinary dysfunction associated with prostatic hyperplasia, the urinary dysfunction is generated by both urethral stricture (mechanical obstruction) caused by compression of enlarged prostate and over-shrinkage (functional obstruction) of smooth muscle of prostate accompanied by an increase in α1 receptors in the enlarged prostate (cf. *Rinsho Kagaku*, 33(12):1542, 1997).

On the other hand, neurogenic bladder is a general term for abnormal urination caused by disorder of sympathetic nerve, parasympathetic nerve, etc. controlling the action of bladder and urethra but it does not stand for localizing and systematic diseases (cf. "Hyojun Hinyoki Kagaku", the fifth edition, published in 1998)

Main diseases which cause neurogenic bladder are (1) encephalopathy such as dementia, cerebrovascular disturbance, cerebral wound, encephalitis, brain tumor, multiple sclerosis. Parkinson disease, Shy-Grager syndrome and olivopontocerebellar atrophy, (2) spondylopathy such as spinal cord injury, spinal cord tumor, spondylitis, myelopathy, vascular disease of spinal cord, spinal cord diseases (such as cervical spondylosis, disk herniation and cervical ossification of posterior longitudinal ligament), spina bifida and multiple sclerosis and (3) peripheral nerve disturbance such as diabetes mellitus, operations in pelvic cavity (for radical therapy of uterine cancer and rectum cancer), spinal cord diseases (such as disk herniation, spinal cord stenosis, lumbar separation and spondylolisthesis), Guillan-Barre syndrome, pelvic fracture and cauda equina nerve tumor.

In the urinary dysfunction associated with neurogenic bladder, there are a voiding dysfunction and a strange dysfunction and each of those dysfunction may take place either independently or jointly depending upon phase, site, etc. of the dysfunction. In the voiding dysfunction, symptoms such as retardation of initiation of urination, prolongation of time for urination, intermittent urination, minute urinary stream, etc. appear.

At present, the drugs where the effectiveness in clinic has been confirmed as a therapeutic agent for voiding dysfunction associated with neurogenic bladder in Japan, Europe and U. S. A. are cholinergic drugs only and their effect is to improve the, urinary disturbance by recovering the shrinking force of bladder of a low active type where detrusor reflex is lost.

Since there is no animal model for reflecting the symptom in neurogenic bladder, development of the therapeutic drugs therefor is difficult and, even if a few effective cases were clinically confirmed in some substances other than the above-mentioned cholinergic drugs, no drug which can be competent for practical use an the drug has been obtained yet.

Investigation has been carried out for a possibility for the therapy of neurogenic bladder based upon an improvement of urinary efficiency by a decrease in urethral resistance by administration of an α-receptor antagonists such as phenoxybenzamine and prazosin hydrochloride to adrenalinergic sympathetic nerve which is abundantly distributed in smooth muscle of neck of urinary bladder and urethra of prostate. However, there has been almost no success as a drug which can be competent in clinic.

There has been a demand for developing a therapeutic drug having a new action mechanism which can be, competent in practical use as a therapeutic agent for voiding dysfunction associated with neurogenic bladder.

DISCLOSURE OF THE INVENTION

Under such circumstances, the present inventors have found that tamsulosin or a salt thereof is effective for the therapy of voiding dysfunction of the patients with neurogenic bladder.

Thus, the present invention relates to a pharmaceutical composition for the therapy or voiding dysfunction associated with neurogenic bladder where the composition contains tamsulosin or a pharmaceutically acceptable salt thereof as an effective component.

The present invention further relates to the use of tamsulosin or a pharmaceutically acceptable salt thereof for the manufacture of a therapeutic agent for voiding dysfunction associated with neurogenic bladder. The present invention furthermore relates to a method for the therapy of voiding dysfunction associated with neurogenic bladder where the method includes administration of a therapeutically effective dose of tamsulosin or a pharmaceutically acceptable salt thereof to a patient.

The chemical name for tamsulosin is (R)(−)-5-{2-{[2-(o-ethoxyphenoxy)ethyl}amino]propyl}-2-methoxybenzenesulfonamide which is represented by the following structural formula. Tamsulosin has been firstly disclosed in the Japanese Laid-Open Patent Publication No.56-210665 together with its pharmaceutically acceptable salts.

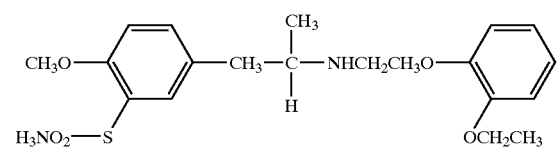

Tamsulosin or a salt thereof has been known to have a blocking action to adrenaline $\alpha_{1A}$ receptor end particularly its hydrochloride (tamsulosin hydrochloride) has been known to have a blocking action to $\alpha_1$ receptor in urethra and prostate and to reduce the prostatic pressure in the urethral inner pressure curve whereby the urinary dysfunction associated with benign prostatic hyperplasia is improved.

However, there has been no report for confirming the effectiveness to voiding dysfunction associated with neurogenic bladder wherein the onset mechanism is different. Now the present inventors have clinically confirmed for the first time that tamsulosin hydrochloride is effective for the therapy of voiding dysfunction associated with neurogenic bladder.

Incidentally, although there have been several reports for the clinical applications to neurogenic bladder by other α-receptor antagonists such as prazosin hydrochloride, bunazosin hydrochloride, moxisylyte and urapidil, there has been no α-receptor antagonist which can be confirmed to be clinically effective an a therapeutic agent for voiding dysfunction associated with neurogenic bladder in Japan, Europe and U. S. A. For example, with regard to bunazosin hydrochloride, an application for additional use for voiding dysfunction associated with neurogenic bladder was filed with the Ministry of Health and Welfare in Japan but no permission was obtained whereby such an attempt has been given up (cf. *Asu no Shinyaku*, 1990/Pharma Projects).

The present invention will be further illustrated as hereunder.

Tamsulosin and pharmaceutically acceptable salts thereof are easily available either by the methods mentioned in the Japanese Laid-Open Patent Publications No. 56-110665 and 62-114952 or by the methods similar thereto.

Tamsulosin is able to form pharmaceutically acceptable acid- and base-addition salts with a large extent of inorganic and organic acids and bases. Such salts constitute a part of the present invention as well. Their examples are salts with inorganic acid such as hydrochloric acid, sulfuric acid and phosphoric acid; salts with organic acid much as fumaric acid, malic acid, citric acid and succinic acid: salts with alkali metal such as sodium and potassium; and salts with alkali earth metal such as calcium and magnesium. The most preferred salt in the present invention is a hydrochloride.

The pharmaceutical agents of the present invention can be prepared a solid preparations for oral use, liquid preparations for oral use or injection preparations by conventional methods using organic or inorganic carriers, vehicles or other additives which are suitable for oral or parenteral administration. Preferred forms are solid preparations for oral use which are able to be taken by the patients themselves and also are convenient for storing and carrying and, to be more specific, they are tablets, diluted powder, granules, fine particles, capsules, pill, etc.

In such solid preparations, the active substance is mixed with at least one inert diluent such as lactose mannitol, glucose, microcrystalline cellulose, starch, polyvinylpyrrolidone, magnesium metasilicate aluminate, etc. The composition may contain additives other than the inert diluent by conventional methods such as a binder (e.g. hydroxypropyl cellulose, hydroxypropyl methyl cellulose, etc.), a lubricant (e.g. magnesium stearate, calcium stearate, polyethylene glycol, starch, talc, etc.), a disintegrating agent (e.g., cellulose calcium glycolate), a stabilizer (e.g. lactose), a solubilizing aid (e.g., glutamic acid, aspartic acid, etc.), a plasticizer (e.g. Tween 80, triacetin, etc.) and a coloring agent (e.g. titanium oxide and iron sesquioxide). If necessary, tablets or pills may be coated with a sugar coat or film soluble in stomach or in intestine such as sucrose, gelatin, agar, pectin, hydroxypropyl cellulose, hydroxypropyl methyl cellulose phthalate, etc.

The most preferred form in the present invention is a sustained release preparations of a prolonged release type. Sustained release preparations may be made into tablets, granules, fine particles or capsules by conventional methods. Sustained release preparations are prepared by coating tablets, granules, fine particles or capsules with, for example, fat/oil, polyglycerol fatty acid ester, hydroxypropyl cellulose, etc. by conventional methods.

The sustained release preparation which is disclosed in the Japanese Laid-Open Patent Publication No.62-000009 is particularly preferred. Thus, each unit preparation is prepared in such a manner that a dissolution suppressor is added to a mixture of an active compound and 50% by weight or more of a unit-forming substance in the unit followed by granulating and the resulting particles are filled in a capsule to prepare a capsule preparation or are made into tablets by conventional methods. Crystalline cellulose is preferred as a unit-forming substance. With regard to the dissolution suppressor, water-insoluble high-molecular substance such as acrylate polymer or copolymer or cellulose derivative are used and it in preferred that such a substance is used in a form of an aqueous suspension, an aqueous emulsion or a solution in a water-containing organic solvent. Examples of the commercially available ones are Eudragit L30D-55 (methcrylate copolymer LD). Eudragit B30D (emulsion of copolymer of ethyl acrylate with methyl methacrylate) and Aqua Coat ECD-30 (aqueous suspension of ethyl cellulose) and they are used as dissolution suppressors as they are or after diluting with water if necessary.

The dose of tamsulosin or a pharmaceutically acceptable salt thereof may be appropriately decided for each individual by taking administration route, symptom of the disease, age of the patient to be administered, sex, etc. into consideration in the case of oral administration of tamsulosin hydrochloride, the usual dose in terms of the effective component for adult is usually about 0.1 to 0.8 mg/day or, most preferably, 0.2 to 0.4 mg/day and this is orally administered once daily after a meal.

Although the pharmaceutical agent of the present invention is well effective by a single administration, it is also possible that said agent is used together with a cholinergic drug such as distigmine bromide, bethanechol chloride, etc. or with other central nervous system drugs either simultaneously or with time interval. It is further possible that said agent is used together with a therapeutic agent for causal diseases for neurogenic bladder.

Industrial Applicability

In accordance with the present invention, an excellent therapeutic agent for voiding dysfunction associated with neurogenic bladder where said agent to able to be competent for actual use in clinical field can be offered.

Best Mode for Carrying Out the Invention

The present invention will now be further illustrated by way of the following examples and test examples although the present invention is not limited to those examples, etc.

EXAMPLE 1

Tamsulosin hydrochloride (5 g) and 470 g of crystalline cellulose were well mixed and a mixture of 83.3 g of Eudragit L30D-55 (25 g as a solid) with water to make 500 g was added thereto followed by granulating using a high-speed stirring granulating machine. The resulting particles were spherical having a particle size of 0.1–1.5 mm where most of them were in 0.2–1.0 mm.

The resulting particles were mixed with talc and magnesium stearate and the mixture was filled in capsules to prepare the capsule preparation. (Each capsule contained 0.2 mg of tamsulosin hydrochloride.)

EXAMPLES 2–6

The particles which were manufactured by the same manner an in Example 1 according to the formulations of Table 1 were made into the capsule preparations.

TABLE 1

| | (unit: grams) | | |
|---|---|---|---|
| Example Number | Tamsulosin Hydrochloride (g) | Crystalline Cellulose (g) | Eudragit L30D-55 (Solid Content) (g) |
| 2 | 5 | 445 | 188.8 (80) |
| 3 | 5 | 39.5 | 333.3 (100) |
| 4 | 5 | 482.5 | 41.7 (12.5) |
| 5 | 2.5 | 472.5 | 83.3 (25) |
| 6 | 1.25 | 473.75 | 83.3 (25) |

Tamsulosin hydrochloride (5 g), 420 g of crystalline cellulose and 50 g of magnesium stearate were well mixed and a mixture of 83.3 g of Eudragit L30-D-55 (25 g as a solid) with water to make 500 g was added thereto followed by kneading and granulating using a centrifugal fluidized granulating machine. The resulting particles were spherical having a particle size of 0.1–1.5 mm where most of them were in 0.2–1.0 mm.

The resulting particles were mixed with talc and magnesium stearate and the mixture was filled in capsules to prepare the capsule preparation. (Each capsule contained 0.2 mg of tamsulosin hydrochloride.)

EXAMPLES 8–10

The particles which were manufactured by the same manner as in Example 7 according to the formulations of Table 2 were made into the capsule preparations.

TABLE 2

| | (unit: grams) | | | |
|---|---|---|---|---|
| Example Number | Tamsulosin Hydrochloride | Crystalline Cellulose | Magnesium Stearate | Eudragit L30D-55 (Solid Content) |
| 8 | 6 | 480 | 10 | 83.3 (25) |
| 9 | 5 | 445 | 25 | 83.3 (25) |
| 10 | 2.5 | 482.5 | 10 | 83.3 (25) |

EXAMPLE 11

Hydrogenated castor oil (80 g) was melted, 10 g of tamsulosin hydrochloride and 30 g of lowly-substituted hydroxypropyl cellulose were dispersed therein and the mixture was made into fine particles by means of a spray congealing. The resulting fine particles (60 g) and 440 g of crystalline cellulose were well mixed, 500 g of water were added thereto and the mixture was granulated by a centrifugal fluidized granulating machine.

The resulting particles were mixed with talc and magnesium stearate followed by filling in a capsule to prepare a capsule preparation.

Test Example 1. Clinical Test to Patients of Voiding Dysfunction Associated with Neurogenic Bladder.

Clinical test was carried out under the following conditions to the causes of voiding dysfunction associated with neurogenic bladder.

Patients: Sixty patients diagnosed to be voiding dysfunction associated with neurogenic bladder (excluding the cases where the cause was peripheral diseases).

Used drug and method of administration: Capsule preparation containing 0.2 mg of tamsulosin hydrochloride or placebo capsule was used and two capsules were orally administered after breakfast (once daily) for four weeks.

Test period: (1) Wash-out stage: When any therapeutic drug to the disease was given previously, a wash-out period for seven days or longer before starting the observing stage was provided; (2): Observing stage: The observing stage was three days or longer and, when stabilization of the subjective symptoms were confirmed, the therapeutic stage was started; (3): Therapeutic stage: The therapeutic stage was four weeks (28 days).

Observing Items and Terms:

| Test Items | Wash-Out Stage ≥ 7 Days -10 Days | Observing Stage ≥ 8 Days -3 Days | Therapeutic Stage 0 Day | 2 Weeks | 4 Weeks (Completion) |
|---|---|---|---|---|---|
| Measuring Intracyatic Pressure | ←——————●——→ | | | | |
| Subjective Symptom a*) | | ←—●—→ | | ● | ● |
| Impression by Patients | | | | ● | ● |
| Measuring Urinary Flow + Residual Urine | | ←—●—→ | | ● | ● |
| Blood Pressure + Heart Rate | | ←—●—→ | | | ● |
| Clinical Test | | ←—●—→ | | | ● |
| Side Effect/ Accidental Symptom | | ←————————————————→ | | | |

*) Subjective Symptoms:
(1) Frequency of urination at daytime;
(2) Frequency of urination at night;
(3) Self-catheterization;
(4) Retardation in initiation of urination;
(5) elongation of urination time;
(6) Strain upon urination;
(7) Stoppage of urinary stream;
(8) Vigor or dash of urination;
(9) Frequency of urinary inoontinence.

Method of Evaluation: Evaluation was done according to the following flow chart.

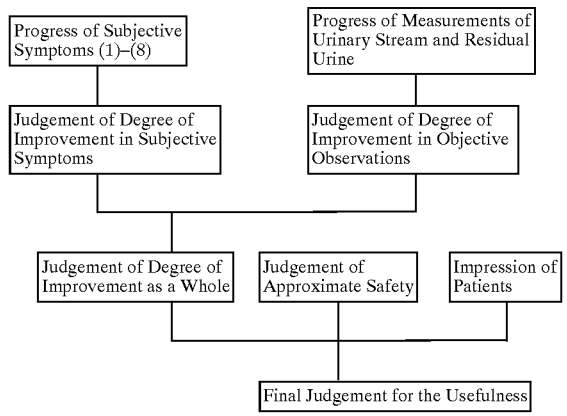

Result: Table 3 shows the progress of the subjective symptoms (1)–(8) in terms of changing rate (decreasing rate) of the total score and the progress of the urinary flow and residual urine in terms of changing amounts of maximum flow stream rate, average urinary flow rate and residual urine rate.

TABLE 3

| | Tamsulosin Hydrochloride- Administered Group | Placebo-Administered Group |
|---|---|---|
| Total Score (Changing Rate) | −31 ± 34.2% (n = 23) | −29 ± 31.9% (n = 22) |

TABLE 3-continued

| | Tamsulosin Hydrochloride- Administered Group | Placebo-Administered Group |
|---|---|---|
| Maximum Urinary Flow (Changing Amt) | 2.5 ± 3.01 ml/sec (n = 16) | −0.6 ± 7.52 ml/sec (n = 15) |
| Average Urinary Flow (Changing Amt) | 1.2 ± 1.66 ml/sec (n = 16) | −0.2 ± 4.26 ml/sec (n = 15) |
| Residual Urine Amount (Changing Amt) | −18 ± 80.1 ml (n = 23) | −55 ± 128.8 ml (n = 15) |
| Residual Urine Rate (Changing Amt) | −13 ± 20.0% (n = 16) | −4 ± 24.1% (n = 15) |

Degrees of improvement in subjective symptoms and objective observation and degree of improvement as a whole were evaluated as significant improvement, medium improvement, light improvement, unchanged and worsening depending upon the above-mentioned result.

Approximate safety was evaluated as no problem, little problems, some problems and problems according to the presence/absence and degree of side effect, change of blood pressure and pulse rate, and abnormal change in clinical date.

Impression by the patient was judged to be much improvement, improvement, some improvement, no change, some worsening, worsening and much worsening.

Finally, degree of improvement as a whole, approximate safety and impression by patient were taken into consideration and the final judgement for the Usefulness wan judged to be any of the five groups—very useful, useful, somewhat useful and not preferable.

With regard to the approximate safety and impression by patient, there was no significant difference between the groups administered with tamsulosin hydrochloride and with placebo.

The result is shown in Table 4.

TABLE 4

| | | Tamsulosin Hydrochloride-Administered Group | Placebo-Administered Group |
|---|---|---|---|
| Degree of Improvement in Subjective Symptoms | ≧Medium Improvement | 43.5% (10/23) | 31.8% (7/22) |
| Degree of Improvement in Objective Observation | ≧Medium Improvement | 80.0% (12/20) | 23.5% (4/17) |
| Degree of Improvement as a Whole | ≧Medium Improvement | 60.0% (12/20) | 23.5% (4/17) |
| Usefulness | ≧Useful | 52.2% (12/23) | 17.8% (3/17) |

Tamsulosin hydrochloride showed significant improvement in the improvement of subjective symptom and objective observation of the patients suffering from voiding dysfunction associated with neurogenic bladder and also in the improvement as a whole. When the impression by the patients was further taken into consideration, it was confirmed that tamsulosin hydrochloride was useful as a therapeutic agent for voiding dysfunction associated with neurogenic bladder.

What is claimed is:

1. A method of treating voiding dysfunction associated with neurogenic bladder, comprising administering tamsulosin or a pharmaceutically acceptable salt to a patient with neurogenic bladder, wherein the patient does not exhibit lower urinary tract obstruction.

2. A method of treating neurogenic bladder comprising administering an effective amount of tamsulosin or a pharmaceutically acceptable salt thereof to a patient with neurogenic bladder.

3. A method of treating voiding dysfunction associated with neurogenic bladder, comprising administering and effective amount of tamsulosin or a pharmaceutically acceptable salt thereof to a patient with neurogenic bladder, wherein said voiding dysfunction is not associated with benign prostatic hypertrophy.

* * * * *

UNITED STATES PATENT AND TRADEMARK OFFICE
CERTIFICATE OF CORRECTION

PATENT NO. : 6,861,070 B1
DATED : March 1, 2005
INVENTOR(S) : Kouji Yoshinaga

It is certified that error appears in the above-identified patent and that said Letters Patent is hereby corrected as shown below:

Column 10,
Lines 20-21, "administering and effective" should read -- administering an effective --.

Signed and Sealed this

Twenty-fourth Day of May, 2005

JON W. DUDAS
*Director of the United States Patent and Trademark Office*